(12) United States Patent
Corbett et al.

(10) Patent No.: US 11,305,105 B2
(45) Date of Patent: Apr. 19, 2022

(54) CANNULA ASSEMBLY

(71) Applicant: Abiomed, Inc., Danvers, MA (US)

(72) Inventors: Scott C. Corbett, Beverly, MA (US); Caitlyn Hastie, Billerica, MA (US)

(73) Assignee: ABIOMED, INC., Danvers, MA (US)

( * ) Notice: Subject to any disclaimer, the term of this patent is extended or adjusted under 35 U.S.C. 154(b) by 0 days.

(21) Appl. No.: 16/242,842

(22) Filed: Jan. 8, 2019

(65) Prior Publication Data
US 2019/0143016 A1 May 16, 2019

Related U.S. Application Data

(63) Continuation of application No. 15/726,888, filed on Oct. 6, 2017, now Pat. No. 10,207,037, which is a continuation of application No. 14/711,451, filed on May 13, 2015, now Pat. No. 9,814,814.

(60) Provisional application No. 61/992,825, filed on May 13, 2014.

(51) Int. Cl.
*A61M 60/857* (2021.01)
*A61M 60/135* (2021.01)
(Continued)

(52) U.S. Cl.
CPC ........ *A61M 60/857* (2021.01); *A61M 60/135* (2021.01); *A61M 60/148* (2021.01);
(Continued)

(58) Field of Classification Search
CPC .... A61M 1/1008; A61M 1/122; A61M 1/125; A61M 1/1034; A61M 1/101;
(Continued)

(56) References Cited

U.S. PATENT DOCUMENTS

| 4,986,814 A | * | 1/1991 | Burney | ............ | A61M 25/0041 |
| | | | | | 604/164.11 |
| 5,314,418 A | | 5/1994 | Takano et al. | | |

(Continued)

FOREIGN PATENT DOCUMENTS

| EP | 1304133 A2 | 4/2003 |
| GB | 2504177 A | 1/2014 |

(Continued)

OTHER PUBLICATIONS

International Search Report and Written Opinion for corresponding International Application No. PCT/US2015/030660 dated Jul. 30, 2015 (10 pages).

(Continued)

*Primary Examiner* — Lindsey G Wehrheim
(74) *Attorney, Agent, or Firm* — Botos Churchill IP Law LLP

(57) ABSTRACT

Cannula assemblies and methods of manufacturing cannula assemblies are provided. The cannula assembly includes a cannula and a pigtail extension coupled to the cannula. The pigtail extension includes a proximal section having a first stiffness and a distal section having a second stiffness, the first stiffness greater than the second stiffness. The proximal section of the pigtail extension is positioned between the cannula and at least a portion of the distal section.

26 Claims, 3 Drawing Sheets

(51) Int. Cl.
　　*A61M 60/148* (2021.01)
　　*A61M 60/205* (2021.01)
　　*A61M 60/414* (2021.01)

(52) U.S. Cl.
　　CPC ......... *A61M 60/205* (2021.01); *A61M 60/414* (2021.01); *A61M 2205/0216* (2013.01); *A61M 2207/00* (2013.01); *Y10T 29/49828* (2015.01)

(58) Field of Classification Search
　　CPC ....... A61M 2205/0216; A61M 2207/00; Y10T 29/49828
　　See application file for complete search history.

(56) References Cited

U.S. PATENT DOCUMENTS

| | | | |
|---|---|---|---|
| 5,725,513 A * | 3/1998 | Ju | A61L 29/049 604/527 |
| 5,766,151 A * | 6/1998 | Valley | A61M 39/0247 604/103.07 |
| 6,007,478 A | 12/1999 | Siess et al. | |
| 9,814,814 B2 | 11/2017 | Corbett et al. | |
| 2004/0064090 A1 | 4/2004 | Keren et al. | |
| 2008/0086027 A1 * | 4/2008 | Siess | A61M 1/101 600/16 |
| 2012/0172655 A1 * | 7/2012 | Campbell | A61M 25/04 600/16 |

FOREIGN PATENT DOCUMENTS

| | | |
|---|---|---|
| JP | H0928808 A | 2/1997 |
| JP | 2008516654 A | 4/2006 |
| WO | 2005016416 A1 | 2/2005 |
| WO | 2006040252 A1 | 4/2006 |

OTHER PUBLICATIONS

Office Action for corresponding European Patent Application No. 15724913.7 dated Jun. 2, 2020 (4 pages).
Office Action for corresponding Canadian Application No. 2,947,985 dated Jul. 16, 2021 (7 pages).

* cited by examiner

CANNULA ASSEMBLY

CROSS-REFERENCE TO RELATED APPLICATIONS

This application is a continuation of U.S. application Ser. No. 15/726,888, filed Oct. 6, 2017 (issued as U.S. Pat. No. 10,207,037), which is a continuation of U.S. application Ser. No. 14/711,451 filed on May 13, 2015 (issued as U.S. Pat. No. 9,814,814), which claims the benefit of U.S. Provisional Application Ser. No. 61/992,825 filed May 13, 2014. The specifications of each of the foregoing applications are incorporated herein by reference in their entirety.

TECHNICAL FIELD

The present disclosure relates to cannula assemblies. More specifically, the present disclosure relates to cannula assemblies implementable with a blood pump assembly, such as an intravascular heart pump system.

BACKGROUND

Blood pump assemblies, such as intracardiac or intravascular blood pumps may be introduced in the heart to deliver blood from the heart into an artery. Blood pump assemblies may be introduced percutaneously during a cardiac procedure through the vascular system. Specifically, blood pump assemblies can be inserted via a catheterization procedure through the femoral artery or the axillary/subclavian artery, into the ascending aorta, across the valve and into the left ventricle. The inserted blood pump assembly pulls blood from the left ventricle of the heart through a cannula and expels the blood into the aorta.

The stability of a blood pump assembly in the ventricle impacts the use and performance of the pump. Positioning a blood pump assembly too close to the ventricle apex can lead to suction and arrhythmia problems. Positioning a blood pump assembly too deep in the ventricle can result in the outlet being on the aortic valve or in the ventricle. Mispositioning the blood pump assembly causes consumption of valuable time as the blood pump assembly is repositioned. The time consumed repositioning the blood pump assembly may be vital as procedures requiring such an implementation impact the sustainability and quality of the life of a patient.

SUMMARY

The systems, methods, and devices disclosed herein provide a cannula assembly for an intravascular blood pump. The cannula assembly includes a cannula coupled to a dual stiffness pigtail extension. The dual stiffness pigtail extension has a relatively stiff proximal section and a relatively soft distal section. The intravascular blood pump may produce thrust forces that compress the cannula assembly against a patient's tissue. The stiff proximal section is stiff enough to substantially resist buckling under such compression (e.g., a hardness of 60, 70, 80, 90, 100 or higher on the Shore D scale). In contrast, the distal portion may be soft and flexible enough so that it does tend to buckle against the patient's tissue (e.g., a hardness of 50, 40, 30, 20 or lower on the Shore D scale). This controlled buckling allows the proximal region of the pigtail extension to substantially maintain its original length so that it can act as a mechanical spacer. This spacing can facilitate the proper positioning of the intravascular blood pump relative to the patient's heart or vasculature. For example, the stiff proximal section may prevent a blood inlet from being too close to a ventricular wall to avoid suctioning tissue. Furthermore, the stiff proximal section may ensure that an outlet of the blood pump is positioned on the opposite side of a valve (e.g., the aortic valve) relative to the inlet. This allows blood to be pumped out of the ventricle to increase cardiac output. At the same time, the relatively soft distal section may reduce trauma to a patient's tissue. For example, the softer material of the distal section may reduce stress locally induced in the patient's tissue. Furthermore, the deformation of the distal section of the pigtail may increase the area over which any force transmitted to the tissue is distributed. As used herein, intravascular refers to a component that is positioned, in whole or in part, in a patient's vasculature, within a patient's heart, or within both. Furthermore, as used herein, dual stiffness refers to a component having at least two sections of differing stiffness.

In some implementations, a kit is provided including a cannula and two or more pigtail extensions having relatively stiff proximal sections of varying lengths (e.g., 10 mm, 20 mm, 30 mm, 40 mm, 50 mm, 60 mm or any other suitable length). Each pigtail extension in the kit has a proximal end portion configured to couple to a distal end portion of the cannula. The coupling may be detachable to allow the physician to change a pigtail extension that is originally coupled to the cannula assembly. This allows a physician to select a pigtail extension that provides the proper spacing for positioning the intravascular blood pump for a particular patient. In some implementations, the appropriate length of the stiff proximal section is determined using imaging (e.g., X-ray, MRI, CT scan, fluoroscopy, or ultrasound) or estimated using patient data (e.g., height, sex, age, or weight).

Various implementations provide blood pump assemblies and methods of manufacturing and implementing blood pump assemblies. Various implementations provide a cannula assembly including a cannula and a pigtail extension coupled to the cannula. The pigtail extension includes a proximal section having a first stiffness and a distal section having a second stiffness, the first stiffness greater than the second stiffness. The proximal section of the pigtail extension is positioned between the cannula and at least a portion of the distal section.

In particular implementations, the cannula assembly includes a pump coupled to the cannula. The cannula is positioned between the pump and the pigtail extension. The cannula assembly may include an impeller blade rotatably coupled to the pump motor. The impeller blade is positioned at least in part in the pump housing component, in accordance with particular implementations. The pump is coupled to the cannula by a pump housing component including a plurality of blood exhaust apertures, in accordance with particular implementations. In particular implementations, the pump housing component includes a peripheral wall extending about a rotation axis of the impeller blade. The peripheral wall includes a plurality of blood exhaust apertures; each blood exhaust aperture in the plurality of blood exhaust apertures is encircled by a circumferential aperture edge. The circumferential aperture edge extends across the peripheral wall from an inner peripheral wall surface to an outer peripheral wall surface. The circumferential aperture edge includes a rounded edge portion, rounded between the inner peripheral wall surface and the outer peripheral wall surface, in accordance with particular implementations. The cannula component may include a blood inlet manifold. The blood inlet manifold may include a plurality of inlet openings. In particular implementations, the proximal section of the pigtail extension is composed of nylon. In particular implementations, the proximal section of the pigtail extension is composed of a polymer including, but not limited, to one or more of polyurethane or pebax. In particular implementations, the distal section of the pigtail extension is composed of pebax. In particular implementations, the distal section of the pigtail extension is composed of a polymer including, but not limited to, polyurethane. The proximal section of the pigtail extension may have a hardness or durometer in the range of 60-100 Shore D. The distal section of the pigtail extension may have a hardness or durometer in the range of 20-50 Shore D. The stiffness of the proximal portion may be altered by the addition of other materials such as glass filler or metal or fiber braids.

Various implementations provide a method of manufacturing a cannula assembly. The method includes coupling a pigtail extension to a cannula. The pigtail extension includes a proximal section having a first stiffness and a distal section having a second stiffness that is less than the first stiffness. The proximal section is positioned between the cannula and at least a portion of the distal section. The method also includes coupling a pump to the cannula. The cannula is positioned between the pump and the pigtail extension.

In particular implementations, an impeller blade is rotatably coupled to the pump motor. The impeller blade is positioned at least in part in the pump housing component, in accordance with particular implementations. The pump is coupled to the cannula by a pump housing component including a plurality of blood exhaust apertures, in accordance with particular implementations. The pigtail extension may be coupled to the cannula via a blood inlet manifold. The blood inlet manifold may include a plurality of inlet openings. In particular implementations, the proximal section of the pigtail extension is composed of nylon. In particular implementations, the proximal section of the pigtail extension is composed of a polymer including, but not limited to, one or more of polyurethane or pebax. In particular implementations, the distal section of the pigtail extension is composed of pebax. In particular implementations, the distal section of the pigtail extension is composed of a polymer including, but not limited to, polyurethane.

Variations and modifications will occur to those of skill in the art after reviewing this disclosure. The disclosed features may be implemented, in any combination and subcombination (including multiple dependent combinations and sub-combinations), with one or more other features described herein. The various features described or illustrated above, including any components thereof may be combined or integrated in other systems. Moreover, certain features may be omitted or not implemented. It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

BRIEF DESCRIPTION OF THE DRAWINGS

The skilled artisan will understand that the drawings primarily are for illustrative purposes and are not intended to limit the scope of the subject matter described herein. The drawings are not necessarily to scale; in some instances, various aspects of the subject matter disclosed herein may be shown exaggerated or enlarged in the drawings to facilitate an understanding of different features. In the drawings, like reference characters generally refer to like features (e.g., functionally similar and/or structurally similar elements).

The features and advantages of the inventive concepts disclosed herein will become more apparent from the detailed description set forth below when taken in conjunction with the drawings.

DETAILED DESCRIPTION

Following below are more detailed descriptions of various concepts related to, and implementations of, inventive systems and methods of providing a cannula assembly. It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

The systems, methods, and devices disclosed herein provide a cannula assembly for an intravascular blood pump. The cannula assembly includes a cannula coupled to a dual stiffness pigtail extension. The dual stiffness pigtail extension has a relatively stiff proximal section and a relatively soft distal section. The intravascular blood pump may produce thrust forces that compress the cannula assembly against a patient's tissue. The stiff proximal section is stiff enough to substantially resist buckling under such compression (e.g., a hardness of 60, 70, 80, 90, 100 or higher on the Shore D scale). In contrast, the distal portion may be soft and flexible enough so that it does tend to buckle against the patient's tissue (e.g., a hardness of 50, 40, 30, 20 or lower on the Shore D scale). This controlled buckling allows the proximal region of the pigtail extension to substantially maintain its original length so that it can act as a mechanical spacer. This spacing can facilitate the proper positioning of the intravascular blood pump relative to the patient's heart or vasculature. For example, the stiff proximal section may prevent a blood inlet from being too close to a ventricular wall to avoid suctioning tissue. Furthermore, the stiff proximal section may ensure that an outlet of the blood pump is positioned on the opposite side of a valve (e.g., the aortic valve) relative to the inlet. This allows blood to be pumped out of the ventricle to increase cardiac output. At the same time, the relatively soft distal section may reduce trauma to a patient's tissue. For example, the softer material of the distal section may reduce stress locally induced in the patient's tissue. Furthermore, the deformation of the distal section of the pigtail may increase the area over which any force transmitted to the tissue is distributed. As used herein, intravascular refers to a component that is positioned, in whole or in part, in a patient's vasculature, within a patient's heart, or within both. Furthermore, as used herein, dual stiffness refers to a component having at least two sections of differing stiffness.

Figure 1:
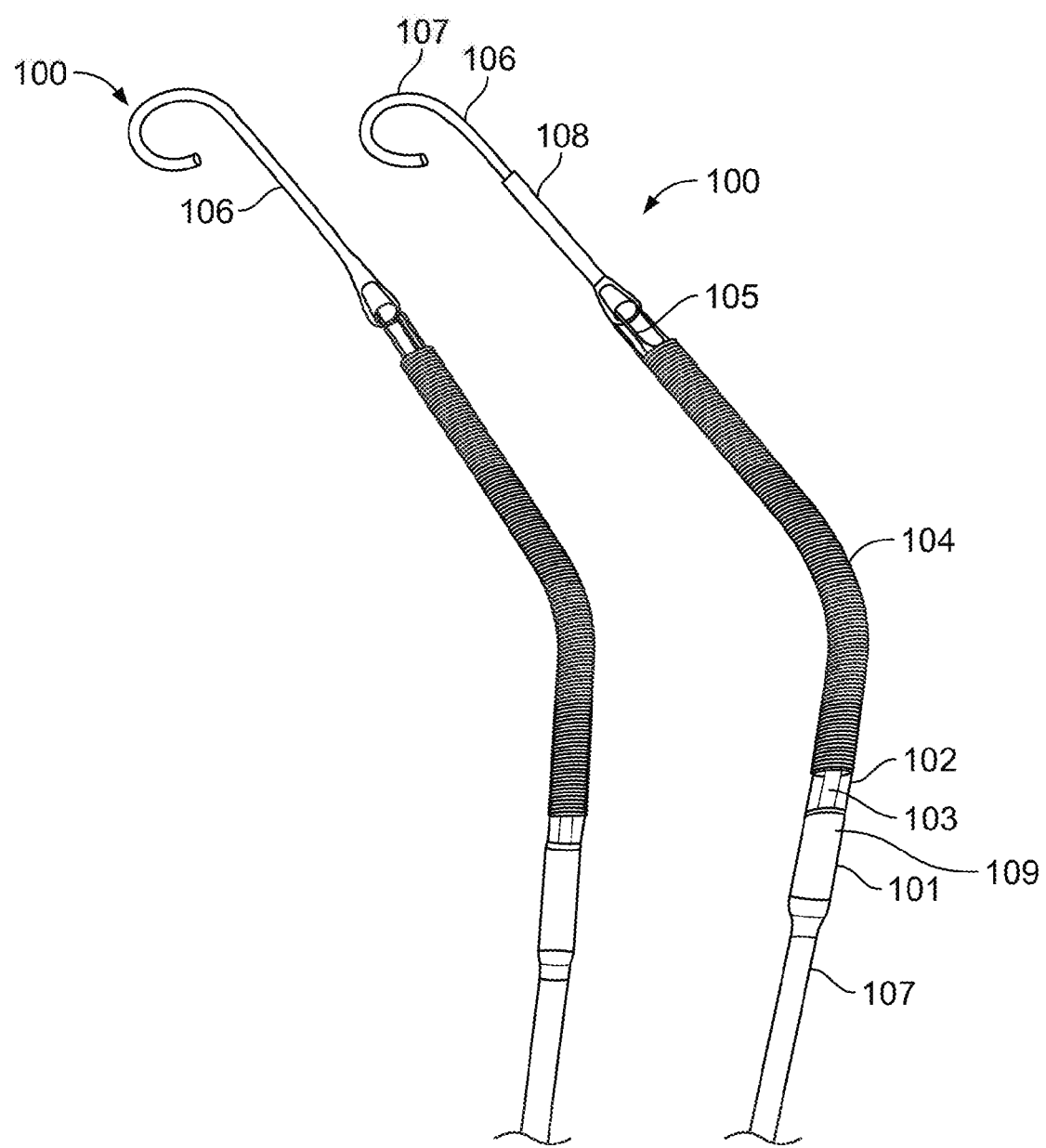
FIG. 1 shows a view of a cannula assembly, in accordance with example implementations.

FIG. 1 shows a view of a blood pump assembly, in accordance with example implementations. The blood pump assembly 100 includes a blood pump 101, a housing component 102, an impeller blade 103 rotatably coupled to the blood pump 101, a cannula 104, a blood inlet manifold 105, a pigtail extension 106, and a catheter 107. The blood pump 101 is coupled to the cannula 104 by the housing component 102 at a distal end of the cannula 104. The blood pump 101 is also coupled to the catheter 107. In some implementations, the blood pump 101 includes a motor. In such cases, the catheter 107 may house electrical lines communicably coupling the pump 101 to one or more electrical controllers or other sensors. In certain implementations, the pump 101 is driven by a flexible shaft. In such cases, the drive portion of the motor may be located outside of the patient's body, and the catheter 107 may house the flexible shaft. The catheter 107 may also house other components, such as a purge fluid conduit, or other conduits configured to receive a guidewire or other procedure related components. The housing component 102 includes one or more apertures or openings 109 configured to expel or exhaust blood drawn into the cannula 104 out of the blood pump assembly 100. In particular implementations, the housing component 102 encapsulates the blood pump 101.

In particular implementations, the blood pump 101 includes a micro-axial pump having a pumping capability including, but not limited to, a range of 5 L/min to 2.5 L/min. In particular implementations, the blood pump 101 includes a micro axial pump having a diameter including, but not limited to, a range of 21 Fr to 10 Fr.

The cannula 104 may include an elongated flexible hose portion and may include a shape memory coil, such as a nitinol coil. In particular implementations, the cannula 104 is composed, at least in part, of a polyurethane material. In particular implementations, the cannula 104 has a diameter including, but not limited to, a range of 12 Fr to 9 Fr. In particular implementations, the cannula 104 includes a 45° bend. The cannula 104 includes the blood inlet manifold 105 coupled to the cannula 104 at a proximal end of the cannula 104 to receive blood flow into the blood pump assembly 100. The blood inlet manifold 105 includes one or more blood inlet openings positioned in the inlet manifold 105. The blood inlet manifold 105 couples the pigtail extension 106 to the cannula 104.

The pigtail extension 106 assists with stabilizing and positioning the blood pump assembly 100 in the correct position in the left ventricle of a heart. In particular implementations, the pigtail extension has an outer diameter including, but not limited to, a range of 4 Fr-8 Fr. In implementation, the blood pump assembly 100 is inserted percutaneously through the femoral artery or the axillary/subclavian artery and into the left ventricle. When properly positioned, the blood pump assembly 100 delivers blood from the inlet area at the blood inlet manifold 105, which sits inside the left ventricle, through the cannula 104, to the outlet openings of the housing component 102 positioned in the ascending aorta.

In accordance with particular implementations, the pigtail extension 106 is configurable from a straight configuration to a partially curved configuration. FIG. 1 shows the pigtail extension in the curved configuration. The curve is about an axis substantially orthogonal to the central axis of the cannula. In some implementations the curve is greater than 180 degrees (e.g., 200, 220, 240, 260, 270, 300, 320 degrees, or any suitable angle). In some implementations the curve is less than 180 degrees (e.g., 90, 100, 120, 140, 160 degrees or any suitable angle). Accordingly, the pigtail extension 106 may be composed, at least in part, of a flexible material. The pigtail extension 106 has a dual stiffness. In particular, the pigtail extension 106 includes a distal section 107 and a proximal section 108, wherein the proximal section 108 is composed of a material having a higher stiffness than the distal section 107. The proximal section 108 may be composed of a different material and may have a different structure than the blood inlet manifold 105 and the cannula 104. In certain implementations, the proximal section 108 is stiff enough to substantially prevent section 108 from buckling, thereby spacing the blood inlet openings in the blood inlet manifold 105 away from the ventricle apex of the heart. The stiffness of proximal section 108 also reduces the probability of the blood outlet openings or blood exhaust apertures 109 in the housing component 102 moving into the aortic valve of the heart or into the ventricle of the heart. The distal section 107 of the pigtail extension 106 is flexible compared to the proximal section 108 to provide an atraumatic tip for contact with the ventricle wall. The flexibility also allows a guidewire to be inserted through an inner conduit 210 of the pigtail extension 106. In particular implementations, the proximal section 108 and the distal section 107 of the pigtail extension are composed of different materials having different stiffness. In certain implementations, the proximal section 108 and the distal section 107 of the pigtail extension are composed of the same material having different stiffness.

In some implementations, the length of the proximal section 108 of the pigtail extension is selected based on the size of a left ventricle of a specific patient. For example, a physician may be provided with a kit including two or more pigtail extensions having stiff proximal sections of varying lengths. Each pigtail extension in the kit may have a proximal end portion that is configured to couple to the cannula (e.g., at the blood inlet manifold 105). In particular, the proximal end portion of the pigtail extension may be configured for detachable coupling to the cannula. For example, the proximal end portion of the pigtail extension may include a snap connection, an interference fit, a screw type connector, or any other suitable reversible or detachable connector. This allows the physician to change the pigtail extension originally coupled to the cannula, while the connection to the pigtail extension is also secure enough to prevent disconnection within the patient's vasculature. In certain implementations, this allows the kit to initially include a cannula having a "standard" sized pigtail initially coupled to the catheter 104 that can be exchanged for a larger or smaller pigtail size as needed. The "standard" pigtail extension can be sized to accommodate a significant portion of patients (e.g., 30%, 40%, 50%, 60%, 70%, 80%, 90%, or 95%), while the larger or smaller sizes may accommodate the remainder of patients. The physician may select the pigtail extension having a proximal section of the appropriate length based on medical imaging. For example, the physician may use MRI, CT, X-ray, ultrasound, fluoroscopy or any other suitable imaging technique, to determine ventricle size. In certain implementations this size is determined pre-operatively. In some implementations, the physician estimates the ventricle size using patient data (e.g., age, height, weight, sex).

Figure 2:
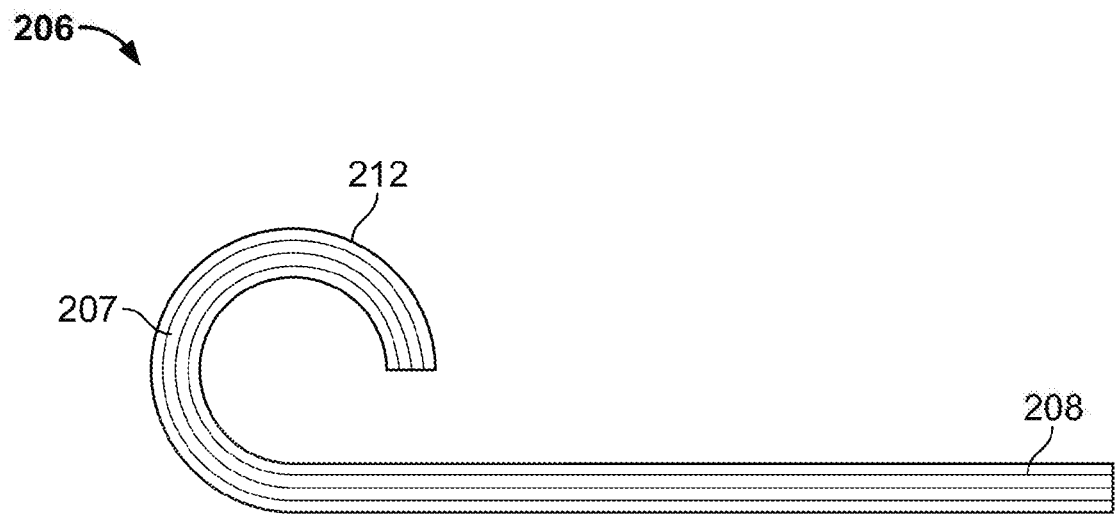
FIG. 2 shows a sectional side view of a pigtail extension, in accordance with example implementations.
Figure 3:
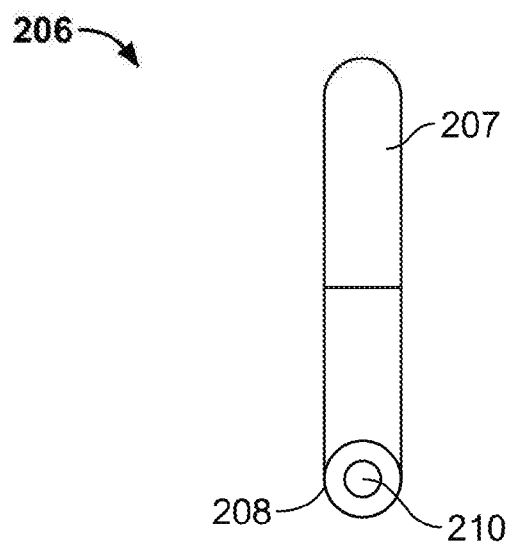
FIG. 3 shows an end view of the pigtail extension of FIG. 2.

FIG. 2 shows a sectional side view of a pigtail extension 206, in accordance with example implementations. FIG. 3 shows an end view of the pigtail extension 206 of FIG. 2. The pigtail extension 206 includes a proximal section 208, a distal section 207 including a curved tip 212, and a conduit 210 for use with a guidewire. The pigtail extension 206 has a dual stiffness because the proximal section 208 has a greater stiffness than the distal section 207. In example implementations, the distal section 207 and the proximal section 208 are composed of one or more layers of materials provided to give the two sections different stiffness. In certain implementations, the proximal section and the distal section have a corresponding diameter. For example, the proximal section 208 may be composed of a single layer of a first material having a first thickness and a first stiffness, and the distal section 207 may be composed of two layers of material. In such cases, the two layers may include a first layer of the first material at a second thickness less than the first thickness and a second layer of a second material at a third thickness (the second and third thickness in aggregate corresponding to the first thickness) and at a second stiffness. Accordingly, the distal section 207 has an overall lower stiffness than the proximal section 208 and may specifically be configured to curl or buckle. The stiff proximal section 208 is stiff enough to substantially resist buckling under such compression (e.g., a hardness of 60, 70, 80, 90, 100 or higher on the Shore D scale). The distal portion 207 is soft and flexible enough so that it does tend to buckle against the patient's tissue (e.g., a hardness of 50, 40, 30, 20 or lower on the Shore D scale).

In some implementations the proximal section may be of greater stiffness than the distal section due to the incorporation of additional materials, such as metals, fibers, braided metal or fiber, glass or any other suitable material, into the proximal section. The additional materials may be added by injection molding, coextrusion, bonding, a thermal reflow process, or any other suitable process. In some implementations the additional materials form a matrix or other suitable structure within the proximal section. The additional material may extend from the proximal section partially into the distal section to reinforce the transition from the proximal section to the distal section. In particular implementations, the additional materials may be deposited between a first material layer and a second material layer of the stiff proximal section. Incorporation of additional materials into the proximal section allows a difference in stiffness to be achieved using a single base material between the proximal and distal sections. The use of a single base material between the proximal and distal sections may help achieve melting in the transition region between the proximal section and the distal section. This may facilitate the joining of the proximal section to the distal section during manufacture.

The intravascular or intracardiac blood pump may produce thrust forces that compress the cannula assembly against a patient's tissue, and the stiffness of the proximal portion allows the proximal region to maintain its original length and act as a mechanical spacer to maintain proper positioning of the blood intravascular pump. Thus, the stiff proximal portion 208 may prevent a blood inlet from being too close to a ventricular wall to avoid suctioning tissue. The stiff distal portion 208 may ensure that an outlet of the blood pump (e.g., blood pump 101) is positioned on the opposite side of a valve (e.g., the aortic valve) relative to the inlet. This allows blood to be pumped out of the ventricle to increase cardiac output. At the same time, the relatively soft distal region may reduce trauma to a patient's tissue. For example, the softer material of the distal section may reduce stress locally induced in the patient's tissue. Furthermore, the deformation of the distal section of the pigtail may increase the area over which any force transmitted to the tissue is distributed.

In particular implementations, the pigtail extension 206 includes a curved tip 212. In some implementations the pigtail extension 206 is configurable from a straight configuration to a partially curved configuration. The curve of the curved tip is about an axis substantially orthogonal to the central axis of the cannula. In some implementations the curve is greater than 180 degrees (e.g. 200, 220, 240, 260, 270, 300, 320 degrees, or any suitable angle). In particular implementations the curve is less than 180 degrees (e.g., 90, 100, 120, 140, 160 degrees or any suitable angle).

The pigtail extension 206 also includes the conduit 210 extending through the proximal section and the distal section. The conduit 210 is sized to receive a guidewire through the pigtail extension 206. In particular implementations, the proximal section 208 of the pigtail extension 206 is composed of nylon. In some implementations, the proximal section 208 of the pigtail extension 206 is composed of a polymer including, but not limited to, one or more of polyurethane or pebax. In particular implementations, the distal section 207 of the pigtail extension 206 is composed of pebax. In certain implementations, the distal section 207 of the pigtail extension 208 is composed of a polymer including, but not limited to, polyurethane. The proximal section 208 of the pigtail extension 206 may have a hardness or durometer in the range of 60-100 Shore D. The distal section 207 of the pigtail extension 208 may have a hardness or durometer in the range of 20-50 Shore D. In accordance with particular implementations, the distal section 207 of the pigtail extension 206 includes 25-75% of the total length of the pigtail extension 206.

Figure 4:
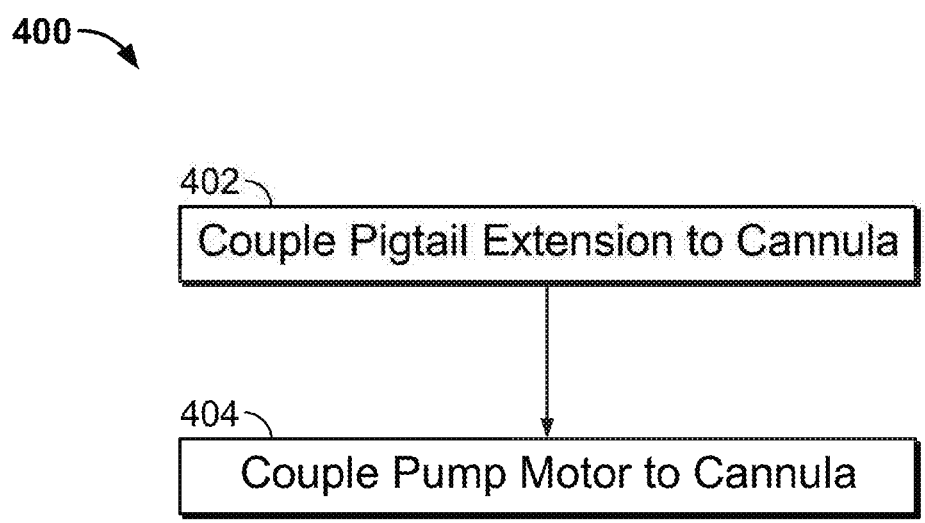
FIG. 4 depicts a method of manufacturing a cannula assembly, according to certain implementations.

FIG. 4 depicts a method 400 for the manufacture of a cannula assembly according to certain implementations. The method 400 may be implemented to manufacture the cannula assembly 100 in any of the aforementioned implementations. In step 402, a dual stiffness pigtail extension, such as the pigtail extensions 106 or 206 of FIGS. 1 and 2, is coupled to the cannula. The pigtail extension includes a relatively stiff proximal section and a relatively flexible distal section. The pigtail extension may be detachably coupled to the cannula or the pigtail extension may be permanently coupled to the cannula. In step 404, a pump is coupled to the cannula such that the cannula is positioned between the pump and the pigtail extension.

As utilized herein, the terms "approximately," "about," "substantially" and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described without restricting the scope of these features to the precise numerical ranges provided. Accordingly, these terms should be interpreted as indicating that insubstantial or inconsequential modifications or alterations of the subject matter described and are considered to be within the scope of the disclosure.

For the purpose of this disclosure, the term "coupled" means the joining of two members directly or indirectly to one another. Such joining may be stationary or moveable in nature. Such joining may be achieved with the two members or the two members and any additional intermediate members being integrally formed as a single unitary body with one another or with the two members or the two members and any additional intermediate members being attached to one another. Such joining may be permanent in nature or may be removable or releasable in nature.

It should be noted that the orientation of various elements may differ according to other exemplary implementations, and that such variations are intended to be encompassed by the present disclosure. It is recognized that features of the disclosed implementations can be incorporated into other disclosed implementations.

It is important to note that the constructions and arrangements of apparatuses or the components thereof as shown in the various exemplary implementations are illustrative only. Although only a few implementations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter disclosed. For example, elements shown as integrally formed may be constructed of multiple parts or elements, the position of elements may be reversed or otherwise varied, and the nature or number of discrete elements or positions may be altered or varied. The order or sequence of any process or method steps may be varied or re-sequenced according to alternative implementations. Other substitutions, modifications, changes and omissions may also be made in the design, operating conditions and arrangement of the various exemplary implementations without departing from the scope of the present disclosure.

While various inventive implementations have been described and illustrated herein, those of ordinary skill in the art will readily envision a variety of other mechanisms and/or structures for performing the function and/or obtaining the results and/or one or more of the advantages described herein, and each of such variations and/or modifications is deemed to be within the scope of the inventive implementations described herein. More generally, those skilled in the art will readily appreciate that, unless otherwise noted, any parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive implementations described herein. It is, therefore, to be understood that the foregoing implementations are presented by way of example only and that, within the scope of the appended claims and equivalents thereto, inventive implementations may be practiced otherwise than as specifically described and claimed. Inventive implementations of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, the technology described herein may be implemented as a method, of which at least one example has been provided. The acts performed as part of the method may be ordered in any suitable way unless otherwise specifically noted. Accordingly, implementations may be constructed in which acts are performed in an order different than illustrated, which may include performing some acts simultaneously, even though shown as sequential acts in illustrative implementations.

The indefinite articles "a" and "an," as used herein in the specification and in the claims, unless clearly indicated to the contrary, should be understood to mean "at least one." As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of" will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one implementation, to at least one, optionally including more than one, A, with no B present (and optionally including elements other than B); in another implementation, to at least one, optionally including more than one, B, with no A present (and optionally including elements other than A); in yet another implementation, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to.

The claims should not be read as limited to the described order or elements unless stated to that effect. It should be understood that various changes in form and detail may be made by one of ordinary skill in the art without departing from the spirit and scope of the appended claims. All implementations that come within the spirit and scope of the following claims and equivalents thereto are claimed.

We claim:

1. A cannula assembly for an intravascular heart pump system comprising:
   a cannula; and
   a pigtail extension coupled to a distal end of the cannula, the pigtail extension including:
      a proximal section having a first stiffness and a length, and
      a distal section having a second stiffness;
   wherein the proximal section incorporates at least one material configured such that the first stiffness is greater than the second stiffness;
   wherein the first stiffness is configured such that, when the cannula is inserted into a heart, the proximal section substantially maintains its length to position the cannula within the heart; and
   wherein the proximal section is positioned between the distal end of the cannula and at least a portion of the distal section.

2. The cannula assembly of claim 1, wherein the proximal section of the pigtail extension has a hardness in the range of about 60 to 100 Shore D.

3. The cannula assembly of claim 1, wherein the distal section of the pigtail extension has a hardness in the range of about 20 to 50 Shore D.

4. The cannula assembly of claim 1, wherein the distal section includes a curved portion.

5. The cannula assembly of claim 4, wherein the curved portion is curved about an axis substantially orthogonal to a central axis of the cannula.

6. The cannula assembly of claim 5, wherein the curved portion is curved by more than about 180 degrees.

7. The cannula assembly of claim 1, wherein the first stiffness is such that the proximal section has a buckling load greater than a thrust force generated by the intravascular heart pump system.

8. The cannula assembly of claim 7, wherein second stiffness is such that the distal section has a buckling load less than a thrust force generated by the intravascular heart pump system.

9. The cannula assembly of claim 1, wherein the proximal section of the pigtail extension has a length of greater than about 10 mm.

10. The cannula assembly of claim 1, wherein the pigtail extension is configured to detachably couple to the cannula.

11. The cannula assembly of claim 1, wherein the distal section of the pigtail extension is between about 25% and 75% of a total length of the pigtail extension.

12. The cannula assembly of claim 1, further comprising a pump coupled to the cannula, the cannula positioned between the pump and the pigtail extension.

13. The cannula assembly of claim 1, wherein the pump is coupled to the cannula by a pump housing component including a plurality of blood exhaust apertures.

14. The cannula assembly of claim 1, wherein the cannula includes a blood inlet manifold.

15. The cannula assembly of claim 1, wherein the proximal section of the pigtail extension is composed of nylon.

16. The cannula assembly of claim 1, wherein the proximal section of the pigtail extension is composed of a polymer including one or more of polyurethane and pebax.

17. The cannula assembly of claim 1, wherein the distal section of the pigtail extension is composed of pebax.

18. The cannula assembly of claim 1, wherein the distal section of the pigtail extension is composed of polyurethane.

19. The cannula assembly of claim 1, wherein the proximal section includes a first layer and a second layer and the at least one material is deposited between the first layer and the second layer.

20. The cannula assembly of claim 1, wherein the at least one material comprises one or more of a metal, a fiber, or a glass.

21. The cannula assembly of claim 1, wherein the at least one material is incorporated into the proximal section by one of injection molding, coextrusion, bonding, or a thermal reflow process.

22. The cannula assembly of claim 1, wherein the at least one material forms a matrix within the proximal section.

23. The cannula assembly of claim 1, wherein the at least one material extends from the proximal section partially into the distal section to reinforce a transition from the proximal section to the distal section.

24. The cannula assembly of claim 1, wherein the proximal section and distal section are formed from a single base material and the at least one material is incorporated into the single base material at the proximal section.

25. A method of manufacturing a cannula assembly for an intravascular heart pump system, the method comprising:
coupling a pigtail extension to a distal end of the cannula, the pigtail extension including a proximal section having a first stiffness and a distal section having a second stiffness, the proximal section positioned between the distal end of the cannula and at least a portion of the distal section, wherein the proximal section incorporates at least one material configured such that the first stiffness is greater than the second stiffness; and
coupling a pump to the cannula, the cannula positioned between the pump and the pigtail extension, wherein the first stiffness is configured such that, when the cannula is inserted into a heart, the proximal section to substantially maintains its length to position the cannula within the heart.

26. The method of claim 25, wherein the proximal section of the pigtail extension has a hardness in the range of 60-100 Shore D.

* * * * *